US011066502B2

(12) United States Patent
Ulmer et al.

(10) Patent No.: US 11,066,502 B2
(45) Date of Patent: Jul. 20, 2021

(54) MALEATE-BASED COPOLYMERS AND METHODS FOR PREPARING THE SAME

(75) Inventors: Herbert Wilhelm Ulmer, Bussum (NL); Theodorus Adrianus Cornelius Flipsen, Groningen (NL)

(73) Assignee: PolyVation Cosmeterials B.V., Groningen (NL)

( * ) Notice: Subject to any disclaimer, the term of this patent is extended or adjusted under 35 U.S.C. 154(b) by 1907 days.

(21) Appl. No.: 13/381,712

(22) PCT Filed: Jul. 2, 2009

(86) PCT No.: PCT/NL2009/050394
§ 371 (c)(1),
(2), (4) Date: Feb. 7, 2012

(87) PCT Pub. No.: WO2011/002278
PCT Pub. Date: Jan. 6, 2011

(65) Prior Publication Data
US 2012/0130036 A1    May 24, 2012

(51) Int. Cl.
*C08F 226/10* (2006.01)
*A61K 8/81* (2006.01)
*A61Q 19/00* (2006.01)
*C08F 222/14* (2006.01)

(52) U.S. Cl.
CPC ............ *C08F 226/10* (2013.01); *A61K 8/817* (2013.01); *A61Q 19/00* (2013.01); *C08F 222/14* (2013.01)

(58) Field of Classification Search
CPC ...... C08F 226/10; C08F 222/14; A61K 8/817; A61Q 19/00
USPC ....................................................... 526/264
See application file for complete search history.

(56) References Cited

U.S. PATENT DOCUMENTS

| | | | |
|---|---|---|---|
| 2,676,949 A * | 4/1954 | Morner | C08F 226/10 508/297 |
| 2,980,654 A | 4/1961 | Perry | |
| 2,980,684 A | 4/1961 | Dunn et al. | |
| 2,999,853 A | 9/1961 | Perry | |
| 3,511,817 A * | 5/1970 | Jasinski | A61K 8/046 106/14.37 |
| 4,057,623 A | 11/1977 | Hase et al. | |
| 5,185,170 A | 2/1993 | Kopolow | |
| 5,191,043 A * | 3/1993 | Shih | C08F 226/10 526/212 |
| 5,466,853 A * | 11/1995 | Koinuma | C07F 9/091 558/158 |
| 5,502,136 A | 3/1996 | Zhong et al. | |
| 5,506,318 A | 4/1996 | Wetzel et al. | |
| 5,786,434 A * | 7/1998 | Ando | C08F 230/08 526/264 |
| 5,919,300 A * | 7/1999 | Burge | C04B 24/165 106/727 |
| 5,959,122 A * | 9/1999 | Ulmer | C07D 207/40 526/270 |
| 6,127,325 A * | 10/2000 | Suyama | C10M 145/14 508/465 |
| 2004/0166081 A1* | 8/2004 | Ulmer | A61K 8/8164 424/70.17 |

FOREIGN PATENT DOCUMENTS

| | | | | |
|---|---|---|---|---|
| GB | 839825 | * | 6/1960 | ................ C08F 2/00 |
| WO | WO 8603501 A1 | | 6/1986 | |

OTHER PUBLICATIONS

Hermanson, "Bioconjugate Techniques", 3rd Ed., Elsevier, p. 190, 2013.

* cited by examiner

*Primary Examiner* — Ling Siu Choi
*Assistant Examiner* — Ronald Grinsted
(74) *Attorney, Agent, or Firm* — Hoffmann & Baron, LLP

(57) ABSTRACT

The invention relates to copolymers of vinyl lactams with derivatized maleates. In particular, it relates to copolymers that are suitably used in the area of personal care and pharmaceuticals, to compositions comprising the copolymers and to methods for preparing the copolymers.

40 Claims, 1 Drawing Sheet

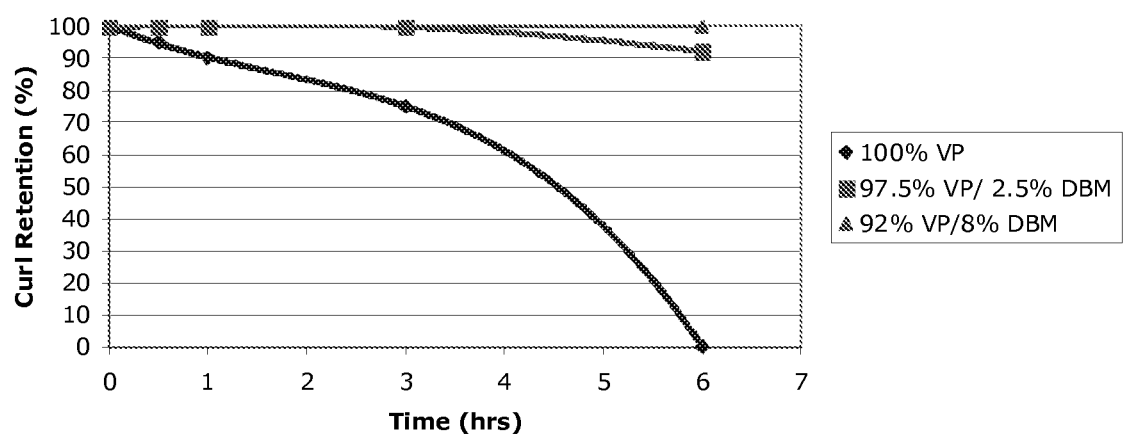
(*) 90% relative humidity (RH), 25° C

MALEATE-BASED COPOLYMERS AND METHODS FOR PREPARING THE SAME

This application is the U.S. National Phase of, and Applicants claim priority from, International Patent Application Number PCT/NL2009/050394 filed 2 Jul. 2009 which is incorporated herein by reference in its entirety.

BACKGROUND OF THE INVENTION

The invention relates to copolymers of vinyl lactams with derivatized maleates. In particular, it relates to copolymers that are suitably used in the area of personal and medical care and pharmaceuticals, to compositions comprising the copolymers and to methods for preparing the copolymers.

Polyvinylpyrrolidone (PVP) is the most famous and most commonly used poly vinyl lactam in commercial use. Due to its excellent toxicological profile and its unique physical and mechanical properties, PVP is used in a host of personal care, pharmaceutical and industrial applications. The homopolymer PVP is highly water-soluble. For some applications, however, it is desirable to utilize a PVP based material that is more oil-soluble. In order to make the PVP less water soluble, a common practice is to copolymerize vinyl pyrrolidone (VP) with a more hydrophobic monomer to give a resultant copolymer that is more hydrophobic, and thus less water-soluble, than the PVP homopolymer.

Examples found in the prior art include the copolymerization of VP with either vinyl acetate (U.S. Pat. No. 5,502,136), hydrophobic acrylates (U.S. Pat. No. 4,057,623) or alpha-olefins (U.S. Pat. No. 5,185,170). Though the resultant polymers described in these patents have reduced water solubility as compared to their PVP homopolymer counterpart, there are significant drawbacks with practicing the aforementioned art.

First and foremost, all the above co-monomers have significantly different reactivities than the VP monomer. As a consequence, the resultant polymerization products are not random copolymers, but actually mixtures of non-homogenous copolymers having a broad compositional make-up. The resultant polymer systems are often actually blends of various polymer compositions that can dissociate and separate from each other and compromise the resultant material properties of the intended polymer. Such properties as film clarity, polymer solubility, film strength, polymer adhesion, etc., can be negatively affected. This can be somewhat overcome by conducting complex feed profiles in which the individual monomers are individually and continuously added to the reaction vessel at varying rates to account for the different monomer reactivities, but this is a rather cumbersome and thus economically undesirable procedure.

Copolymers based on the use of vinyl acetate have the additional drawback in that the synthesized polymers themselves are not chemically stable and rapidly change over time because the acetate unit is readily hydrolysable.

Accordingly, it is an object of this invention to synthesize vinyl lactam—co-derivatized maleate(s) copolymers having controlled solubilities that cover a broad range of solubilities from completely water soluble to completely oil soluble and possess the properties for use as biomaterials in pharmaceutical and personal care applications and raw materials in consumer good and pharmaceutical products.

Another object is to be able to synthesize such polymers easily and simply with the resultant copolymers having a homogenous composition in that the comonomer sequence is randomly distributed over the polymer chain without the need for complicated feed profiles.

SUMMARY OF THE INVENTION

The present inventors recognized the need for an economically attractive synthesis route to prepare copolymers having controlled solubilities that cover a broad range of solubilities, e.g. from completely water soluble to completely oil soluble, and which furthermore possess the properties for use as biomaterials in pharmaceutical, medical and personal care applications and as raw materials in consumer good products. In particular, they set out to prepare a VP-based copolymer which is a) substantially free of undesirable monomers and/or low molecular weight polymer fragments and b) essentially homogenous in its composition in that the comonomer sequence is randomly distributed over the polymer chain. Such polymers are highly sought for in, among others, the area of personal and medical care and pharmaceuticals.

It was surprisingly found that at least some of the above goals could be met by the copolymerization of vinyl lactam monomers and derivatized maleate monomers, wherein the reaction is performed by solution polymerization, and wherein the monomers are fed continuously and simultaneously, e.g. as premixed monomer mixture, to the reaction mixture over a predetermined period of time. By controlling the amount, composition and mixture of derivatized maleates used during the polymerization with the vinyl lactam, a range of vinyl lactam based copolymers having a broad range of resultant solubilities and/or mechanical properties as well as low residual monomer levels can be efficiently synthesized.

The invention therefore provides a method for preparing an N-vinyl lactamcopolymer of the general Formula I

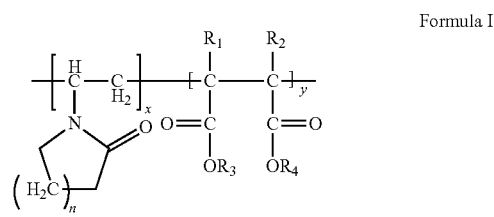

Formula I wherein n=1 or 2, x=about 99-1 mole %, preferably about 99-50 mole %; and y=1-99 mole %, preferably 1-50 mole %, wherein x/y is preferably ≥1.

comprising reacting about 1-99 mole %, preferably 50-99 mole %, of a vinyl lactam monomer (A), and about 99-1 mole %, preferably 50-1 mole %, of a derivatized maleate monomer (B), wherein (A) and (B) are defined according to the following general formula:

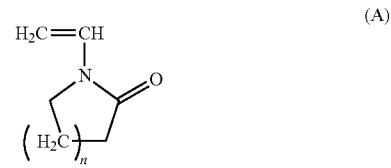

(A)

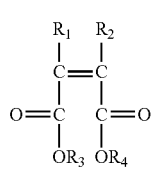

(B)

wherein n is 1 or 2, $R_1$ and $R_2$ are each independently hydrogen or methyl; $R_3$ and $R_4$ are each independently selected from hydrogen, alkyl groups, aryl groups, and heteroalkyl and heteroaryl groups comprising at least one heteroatom other than carbon or hydrogen, with the exception that both $R_3$ and $R_4$ are hydrogen, and wherein said reacting is performed by solution polymerization in a solvent or solvent mixture in which both the lactam monomer (A), the maleate monomer (B) and the resultant copolymer are freely soluble in, and wherein the monomers or a mixture of the monomers is fed, preferably continuously, to the reaction mixture over a predetermined period of time. In one embodiment, the vinyl lactam is vinyl pyrrolidone (n=1). In another embodiment, the vinyl lactam is vinyl caprolactam (n=2).

DESCRIPTION OF THE INVENTION

Vinyl lactam-derivatized maleate copolymers are known in the art. U.S. Pat. Nos. 2,980,654 and 2,999,853 identify copolymers made by the polymerization of VP with dialkyl maleates or fumarates. U.S. Pat. No. 2,980,654 focuses on copolymers that are water-soluble and hexane insoluble. Disclosed is the polymerization of either dialkyl maleates or fumarates via a precipitation polymerization to give the resultant copolymers. In all examples, the polymerization product is precipitated from the hydrocarbon solvent, hexane. Precipitation polymerization is not desirable for the synthesis of copolymers having low residual monomer levels. First of all, the precipitation of the polymer is a heterogeneous process which often leads to preferential fractionation of the polymer based on composition. Secondly, there is significant amount of entrapped monomer in the precipitating polymer which results in high monomer residuals that are difficult to remove/react by usual monomer reduction techniques.

It has been discovered that the polymerization of VP with dialkyl fumarates (DAFs) is not preferred and the resultant polymers made using these monomers are not homogeneous. As will be discussed later, there is no charge complex association of VP with DAFs and the individual monomers possess different reactivities. The different reactivities cause the monomers to be incorporated into the polymer chain in a non-random preference and a polymer product is obtained is actually a mixture of copolymers having a broad compositional make-up. In addition, the reduction of monomer residuals to acceptable levels for use in pharmaceutical and personal care applications is very challenging because each monomer must be handled on an individual basis.

U.S. Pat. No. 2,999,853 focuses on the polymerization of oil-soluble copolymers based on VP and dialkyl maleates and fumarates. In this patent, the polymerization is either conducted in bulk or in the presence of the hydrocarbon solvent, hexane. In all cases, the resultant copolymers obtained are sticky, adhesive-like, viscous liquids. The primary application identified for such materials are for use as industrial pressure sensitive adhesives. As for similar reasons outlined for U.S. Pat. No. 2,980,684, these polymers possess excessive monomer residuals and inferior properties and thus have no application as biomaterials in various pharmaceutical, medical and personal care applications.

It has been discovered by the present inventors that derivatized maleates interact with vinyl lactams to give a weak complex. This weak complex results in a destabilization of the individual double bonds and thus the complex is preferentially polymerized as a "di-monomer" unit. The electron poor double bond of the dialkyl maleate draws electron density from the electron rich double bond of the vinyl lactam. A simple schematic is shown as follows:

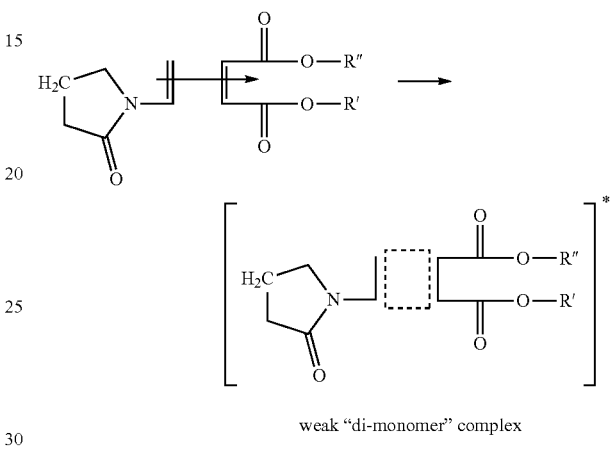

weak "di-monomer" complex

The weak complex promotes the incorporation of the "di-monomer" complex to give a predominantly alternating—vinyl lactam-alt-derivatized maleate—substructure when both monomer species are present. When both monomer sorts are present, the strong preference for an alternating substructure in the resultant polymer greatly reduces the chance that the individual monomers will be incorporated as undesirable blocky segments. Instead, the polymers formed using this technology are generally more homogeneous, meaning the polymer composition over the range of polymer chains is more uniform than if monomer units were used having negligible interaction with each other.

It has also been discovered that the "di-monomer" complex is more reactive to polymerization than either the vinyl lactam or derivatized maleate itself. This activated complex is especially important for promoting the efficient incorporation of derivatized maleates into high molecular weight polymers. If not activated, maleates are relatively difficult to polymerize, especially to significant molecular weights that result in acceptable polymer properties. The activation is also essential in being able to prepare copolymers based on derivatized maleates that possess very low derivatized maleate monomer residual.

Dialkyl fumarates do not undergo this weak complexation with vinyl lactams because the side groups are opposite (trans) to each other. This configuration results in a double bond that is not electron poor in nature because the side group forces cancel each-other out. Because the fumarate double bond is no longer electron poor, no weak complex is formed with the vinyl lactams and there is no tendency for the "di-monomer" to form. Thus, the monomers react as individual species having their own individual reactivity rates to give the resultant polymer. This results in a polymer that is not as homogeneous in chemical composition under similar polymerization conditions as if the corresponding maleate was employed (see example 7 herein below). It should be noted that more complex monomer feed profiles can be initiated in order to synthesize the polymer having a more homogeneous composition, but this approach is less desirable with respect to cost, complexity and robustness when compared to the present invention and in the end would not have the same polymer homogeneity.

The homogeneous copolymers of the invention are obtainable by solution polymerization of the vinyl lactam and derivatized maleate monomers in the presence of a free radical initiator. Any solvent or solvent mixture may be used in which the monomers and resulting copolymer are freely soluble. Suitable solvents include alcohols and esters. For instance, ethanol, isopropanol, ethyl acetate, isopropyl acetate, propane diol, or any mixture thereof, is used. When applicable, the polymerization can be conducted directly in a desired skin care oil, skin care solvent, skin care emulsifier or skin care emollient of natural or synthetic origin. Examples include skin care oils, solvents or emollients selected from the group consisting of natural vegetable oils, natural nut and seed oils, natural based and/or synthetic emulsifiers, natural based and/or synthetic emollients, in particular ester based emollients.

The polymerization reaction can be initiated by means known in the art. Preferred free radical initiators are either organic peroxides or azo initiators such as: t-butyl peroxide, lauroyl peroxide, decanoyl peroxide, t-butyl peroxypivalate, 2,2'-azodi(isobutyronitrile) and 2,2'-azodi(2-methylbutyronitrile), although other initiators known in the art may be used as well.

The monomers are suitably pre-mixed in a suitable solvent and fed over a predetermined time into a pre-heated reaction vessel containing the same solvent as used to dilute the monomer mix. The reaction set-up, monomers, solvent and initiator are typically inerted prior to the start of the polymerization with a gas, such as nitrogen or argon. It is preferred to add the initiator in a continuous fashion in order to best keep the monomer/initiator constant over time. However, the initiator can be added at the start of the reaction and/or during the reaction at multiple fixed amounts if continuous feeding proves too difficult.

According to a preferred embodiment of the invention, the monomers are fed continuously over a predetermined period in the desired ratio, more preferably the monomers are fed continuously as a preformed monomer mixture to the reaction kettle over a predetermined period of time. This ensures that that the desired monomer ratio is held constant over time resulting in a synthesized polymer having the same general compositional make-up. Because the association of vinyl lactam with maleate in solution results in the "activation" of the maleate and increases its reactivity to undergo efficient polymerization, it is important to introduce the monomers in such a way that both species are present during the polymerization process and preferably at a molar ratio of vinyl lactam to maleate of one or greater. This ensures that the maleate is always in the activated state and is efficiently incorporated into the growing polymer chains. At molar ratios of vinyl lactam to maleate of less than one, no longer is all the maleate activated and its efficient incorporation into the polymer chain is compromised, which causes a reduction in resultant polymer molecular weight and homogeneity and generally has a negative effect on polymer properties. For some applications this may be acceptable/desirable such as in oil field exploration, but for applications in medical, cosmetic, consumer and pharmaceutical this is generally undesirable. Polymer purification schemes can be employed to render such polymers acceptable for use, but these are costly and not always successful.

The monomers should be introduced in the reactor in such a way to maximize the association and subsequent maleate activation. It is desirable to add the monomers in a continuous fashion in order to ensure that the monomers are present in the proper concentrations throughout the polymer process and ensure no reacting species are being depleted in an undesirable fashion. Furthermore, the monomer feed time may be selected to provide a desired high copolymer solids level, suitably at least 30 minutes, and generally 1 to 5 hours, depending upon the predetermined feed rate.

Following completion of the addition of the reaction mixture, the reaction is generally allowed to proceed for a period of several additional hours. The total reaction time typically ranges from about 1 hour to about 48 hours, more preferably from about 5 to about 15 hours.

The polymerization reaction is carried out at a suitable temperature, generally about 50°-150° C., preferably 60° C.-100° C. The exact reaction temperature is generally decided by the decomposition rate of the initiator system being used. Generally, reaction temperatures are employed in which the initiator's decomposition half-life is between about 15 minutes and about 5 hours, more preferably between about 1 hour and about 3 hours. Either single initiator or multi initiator systems can be employed in the reaction. Multi initiator systems are often advantages because one initiator is used to react the bulk of the monomer(s) while a higher decomposing temperature initiator is used to react the residual monomer at higher temperatures. In a specific embodiment, a first portion of a monomer mixture in a suitable solvent is heated to a temperature of about 75° C., followed by the continuous yet separate addition of a polymerization initiator and a second portion of the monomer mixture during a predetermined time period, e.g. 1-4 hours. Then, the reaction is allowed to proceed for a further 1-30 hours, preferably 2-10 hours at the same temperature. Then, the temperature may be raised, e.g. to about 80-85° C., and the reactants are allowed to react further under slight reflux for some hours, typically 1-4 hours to react any residual monomer. It can be advantageous to add additional initiator charges to the reaction during this period in order to ensure there is initiator available for the continuous reacting of monomer. Thereafter, the polymer solution thus obtained may be cooled and discharged.

Good results are obtained when the polymerization reaction is conducted at a solids level of between about 10% and 70% solids, preferably 20% to 50%.

A method according to the invention may of course comprise one or more additional steps if desired. In one embodiment, it further comprises the step of exchanging the solvent or solvent mixture used during solution polymerization for a biocompatible solvent. Alternatively, or additionally, the copolymer can be isolated via solvent drying. Both the solvent exchange and solvent drying techniques are known in the art.

A further aspect of the invention relates to an N-vinyl lactam copolymer obtainable by a polymerization method as described herein above. Accordingly, provided is an N-vinyl lactam copolymer of the following structure

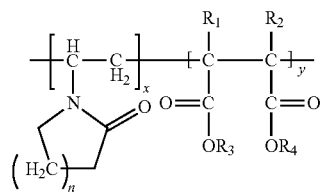

wherein n is 1 or 2, x=99-1 mole %, preferably 99-50 mole % and y=1-99 mole %, preferably 1-50 mole %, in a preferred ratio of x/y≥1; $R_1$ and $R_2$ are each independently hydrogen or methyl, preferably wherein $R_1$ and $R_2$ are both hydrogen, $R_3$ and $R_4$ are each independently selected from hydrogen, alkyl groups, aryl groups, organometallic groups and heteroalkyl and heteroaryl groups comprising at least one heteroatom other than carbon or hydrogen, with the exception that both $R_3$ and $R_4$ are hydrogen, obtainable by reacting about 99-1 mole %, preferably 99-50 mole %, of a vinyl lactam monomer (A), and about 1-99 mole %, preferably 1-50 mole %, of a derivatized maleate monomer (B), wherein (A) and (B) are defined according to the following general formula:

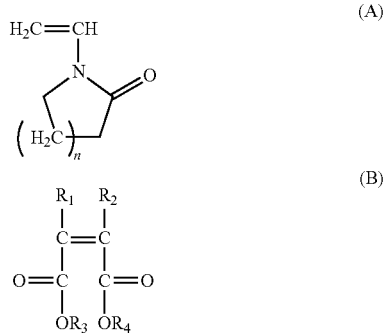

wherein said reacting is performed by solution polymerization in a solvent or solvent mixture in which both the lactam monomer (A), the maleate monomer (B) and the resultant copolymer are freely soluble, and wherein a mixture of the monomers is fed continuously to the reaction mixture over a predetermined period of time.

A copolymer thus obtained is characterized by a low free monomer content, typically less than 1000 ppm, or even less than 500 ppm. The Fikentscher K-value generally ranges from about 10 to about 90, preferably 20-60. The Fikentscher K value is determined by solution viscosity measurements and provides a measure of molecular weight. The correlation between the Fikentscher K value and number average molecular weight (Mn) is as follows: a Fikentscher K value of 50 is roughly equal to a Mn of 28,000 and a Fikentscher K value of 80 is roughly equal to a Mn of 80,000.

The $R_3$ and/or $R_4$ (hetero)alkyl group is for instance a linear or branched alkyl chain, the alkyl chain comprising 1-99, preferably from 1-50 and more preferably from 1-30 carbon atoms. In one embodiment, $R_3$ and/or $R_4$ are selected from the group consisting of substituted or non-substituted alkyl, aryl, arylalklyls, alkoxy, aryloxy, alkylhydroxy, arylhydroxy, alkylaryloxy, alkylamino, arylamino and alkylarylamino groups and organometallic groups, The present inventors discovered that presence of at least one heteroatom in the $R_3$ and/or or $R_4$ side chain of the copolymer has a number of advantages. For instance, it allows to tailor the properties of the polymer according to specific needs. The use of substituents containing one or more heteroatom(s) allows one to introduce more functionality into the resultant copolymer obtained. Many polymer interactions are controlled by the hydrophilic interactions; such as hydrogen bonding, dipole interactions, polar interactions, etc. The derivatization of a polymer with only hydrophobic components only alters the hydrophobic nature of the polymer at the expense of the hydrophilic interactions.

By incorporating heteroatoms into the side chain, one has more flexibility at fine-tuning the resultant forces required in the final copolymer. This ability is essential if the polymer's final use requires interacting with both a hydrophobic element and a hydrophilic element (e.g. polysurfactant). The incorporation of heteroatoms into the side chain also has an effect on the material properties of the resultant copolymer and to drive interactions with hydrophilic surfaces/materials via complexation and/or association.

In one embodiment, the invention provides an N-vinyl lactamcopolymer of the following structure

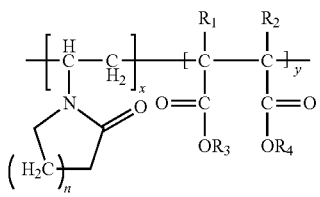

wherein n is 1 or 2, x=about 99-1 mole %, preferably about 99-50 mole % and y=about 1-99 mole %, preferably about 1-50 mole %. Preferably, x/y≥1.

$R_1$ and $R_2$ are each independently hydrogen or methyl, preferably both hydrogen, and wherein $R_3$ and $R_4$ are each independently selected from hydrogen, heteroalkyl and heteroaryl groups comprising at least one heteroatom other than carbon or hydrogen, with the exception that both $R_3$ and $R_4$ are hydrogen.

The at least one heteroatom in a heteroalkyl or heteroaryl group may be selected from the group consisting of oxygen, nitrogen, sulfur, silicon, organometallic and halogens. In one embodiment, $R_3$ and/or $R_4$ are selected from the group consisting of substituted or non-substituted alkoxy, aryloxy, alkylhydroxy, arylhydroxy, alkylaryloxy, alkylamino, arylamino and alkylarylamino groups. Particularly suitable $R_3$ and/or $R_4$ groups comprise a moiety selected from —($CH_2$—$CH_2$—O)—, —($CH_2$—CH($CH_3$)—O)—, —(CH($CH_3$)—$CH_2$—O)—, —($CH_2$—CH($CH_2$—$CH_3$)—O)—, —(CH($CH_2$—$CH_3$)—$CH_2$—O)—, and —(CH($CH_3$)—CH($CH_3$)—O)—. In a further aspect, $R_3$ and/or $R_4$ comprises at least one moiety selected from the group consisting of siloxane, ester, amido, fluoro, amino, organometallic and/or silyl groups.

Of special interest are copolymers wherein at least one of $R_3$ and $R_4$ comprises a charged or chargeable group. In one embodiment, $R_3$ and/or $R_4$ comprises an anionic moiety, preferably selected from the group consisting of carboxylic acid moieties, sulfonic acid moieties, phosphoric acid moieties, betaine moieties, and salts thereof.

In another embodiment, $R_3$ and/or $R_4$ comprises a cationic moiety, preferably selected from the group consisting of amino moieties and ammonium salts. $R_3$ and/or $R_4$ for instance comprises a primary, secondary, tertiary or quaternary amine group.

The following table gives an overview of some of the various chemical structures that are possible for $R_3$ and/or $R_4$. As will be understood, it is in no way a representation of all possibilities, but is merely presented to illustrate the broadness and flexibility of the resultant polymer systems obtainable.

| Structure for $R_3$ and/or $R_4$ | Resultant Functionality | Interactions expected |
|---|---|---|
| —H and corresponding salts due to neutralization | Acid, carboxylate, ionic | Hydrophilic, complexation, neutralization |
| Alkyl: $-(CH_2)_x-CH_3$ where $x = 0-100$, branched and/or linear. | Alkyl | Hydrophobic, associative |
| Hydrolysable sub-unit e.g. $*{+}\underset{H}{\overset{CH_3}{C}}-\underset{\parallel}{\overset{}{C}}-O{+}_n*$ (with C=O) | Hydrolysable sub-unit | Small molecule release, bulk polymer solubility change over time—e.g. water insoluble before hydrolysis, water soluble after hydrolysis |
| $-(CH_2)_n-\langle\text{phenyl}\rangle-R$ <br> aryl derivatives | Aromatic, olefinic | Post cure reactions, association, dipole, aromatic |
| $-C_8H_{16}-=-C_7H_{14}-CH_3$ <br> unsaturated fatty olefins | | |
| $-(CH_2)_2N(C_2H_5)_2$ and salts thereof including zwitterionic and alkyl derivative species on N | Basic, cationic, ionic | Hydrophilic, complexation, neutralization |
| $-(CH_2)_3N(CH_3)_2$ and salts thereof including zwitterionic and alkyl derivative species on N | Basic, cationic, ionic | Hydrophilic, complexation, neutralization |
| $-C_n^{H_{2n}}-N(R)-R$ <br> amine functionality | Basic, ionic | Hydrophilic, complexation, neutralization |
| $-C_n^{H_{2n}}-\overset{R}{\underset{R'}{N^{\oplus}}}-R\ X^{\ominus}$ <br> quarternized amine functionality | Cationic | Hydrophilic, complexation |
| $-C_2H_4-\overset{C_2H_5}{\underset{C_2H_5}{N^{\oplus}}}-C_3H_6-SO_3^{\ominus}$ <br> Zwitterionic functionality | Ionic | Hydrophilic, complexation |
| $-(\overset{H_2}{C}-\overset{H_2}{C}-O)_n-CH_3$ <br> $-(\overset{H_2}{C}-\overset{H}{\underset{CH_3}{C}}-O)_n-CH_3$ <br> ethylene glycol and propylene glycol derivatives | Polar | Hydrophilic |
| $-(\overset{R}{\underset{R}{Si}}-O)_n-R'$ | Silyl | Complexation, functional, hydrophibic/ hydrophilic |

A copolymer of the invention is readily synthesized by reacting a vinyl lactam monomer with the suitable derivatized maleate monomer comprising at least one heteroatom in the $R_3$ and/or $R_4$ group. Preferably, the process according to claim 1 is used. Exemplary derivatized maleate monomers for synthesizing a copolymer include, (N,N-diethylamino)ethyl alkyl maleates, (N,N-dimethylamino)propyl alkyl maleates, quaternary ammonium dialkyl maleates including the cationics: 2-[N,N-diethylammonio)ethyl alkyl maleate chloride, 3-[N,N-dimethylammonio)propyl alkyl maleate chloride, 2-(N,N,N-triethylammonio)ethyl alkyl maleate iodide, 3-[N-ethyl-N,N-dimethylammonio)propyl alkyl maleate iodide, 2-[N-allyl-N,N-diethylammonio)ethyl alkyl maleate bromide, 3-[N-allyl-N,N-dimethylammonio) propyl alkyl maleate bromide, 2-[N,N,N-triethylammonio) ethyl alkyl maleate hydrogen sulfate, 3[N-ethyl-N,N-dimethylammonio]propyl alkyl maleate hydrogen sulfate and the zwitterionics: 2-[N,N-diethyl-N-(3-sulfopropyl)ammonio]ethyl alkyl maleate, 3-[N,N-dimethyl-N-(3-sulfopropyl)ammonio]propyl alkyl maleate; organometallic alkyl maleate, (poly)ethylene glycol alkyl maleates and (poly) propylene glycol alkyl maleates.

In addition to the N-vinyl lactam and derivatized maleate monomers, one or more additional comonomers may be incorporated in the copolymer if desired. The additional comonomer(s) may be added together with the lactam and maleate monomers, for example as part of the monomer mixture. The comonomer may be selected from vinyl acetate, an alpha-olefin, maleic anhydride, a vinyl ether, an acrylate, a methacrylate, an acrylamide, a methylacrylamide and styrene. Accordingly, the invention also provides a copolymer obtainable by reacting a vinyl lactam monomer, a derivatized maleate monomer and one or more additional comonomer(s).

A further aspect relates to a composition comprising at least one N-vinyl lactam copolymer of the invention. Due to their unique properties and association with PVP, copolymers of the invention find their application in various market areas that utilize PVP homopolymers. These applications include: personal care—hair and skin care and color cosmetics, pharmaceuticals—biomaterials for delivery systems, excipients and coatings, and industrial applications—gas hydrate inhibition, paper coatings, textile coatings, ink additive, suspending aid and adhesives. Additional applications include: membrane applications (controlled gas and water permeation), lubricious coatings, compatibilizers, adhesives, polymeric surfactants and antimicrobial and antifouling coatings.

Provided is a personal care composition comprising a copolymer according to the invention, preferably a copolymer having adjustable solubility and mechanical properties. This adjustability is often obtained and balanced by the incorporation of both hydrophilic and hydrophobic chemical elements into the final polymer. Copolymers of special interest contain a hydrophilic amino functionality that can be further modified to give cationic copolymers. Cationic copolymers are attracted to both hair and skin surfaces because both skin and hair are considered anionic surfaces (isoelectric point below pH 6). The cationic copolymers show strong affinity to these natural substrates resulting in excellent film deposition and coating properties. The introduction of long chain hydrophobic aliphatic chains into the copolymer is of considerable interest because these structural elements allows for the fine-tuning of solubility parameters coupled with the conditioning feel attributed to long alkyl group.

The personal care composition can be a hair care composition, like a hair fixative product, hair styling product such as hair gels and hair mousses, hair conditioning product or hair protectant product. Preferred copolymers are based on VP with the monomer family N,N-dialkylamino dialkyl maleates and their respective quarternized ammonio derivatives. Copolymers of VP with dialkyl maleates and long chain alkyl maleates are also highly desirable.

A copolymer is also advantageously used in a skin care composition, such as in water-in-oil or oil-in-water skin creams, day and night creams, eye creams, antiwrinkle creams, moisturizers, bleaching creams, vitamin creams, skin lotions, care lotions, hand and skin disinfectants and/or sanitizers, moisturizing lotions, personal hygiene care compositions, soaps, syndets, liquid washing, shower or bath preparations, nail care compositions, foot care compositions, sunscreens, repellents, shaving compositions, depilatories and anti-acne compositions. Preferred copolymers are based on VP/N,N-dialkylamino dialkyl maleates and their respective ammonio derivatives in which the final copolymer is a polysurfactant. The polysurfactant can be located in either the oil or water phase and can result in conditioning qualities once applied to the skin.

Other uses include the incorporation of the copolymer(s) into a preparation for decorative cosmetics, preferably selected from the group consisting of makeup, mascara, lipsticks, eye shadows, kohl pencils, eyeliners, blushers, powders and eyebrow pencils. Preferred copolymers are oil soluble copolymers in which, for example, VP is polymerized with various dialkyl maleates to give oil soluble polymers having negligible water solubility/affinity.

Also provided herein is a pharmaceutical composition comprising an N-vinyl lactam copolymer according to the invention. For instance, the copolymer(s) may be present in a drug tablet coating or as excipients, or it is used for the delivery of actives or drugs. Copolymers having reduced water solubility and increased flexibility when compared to PVP homopolymer are of interest. This can be quite easily addressed by the synthesis of copolymer based on VP and dialkyl maleates. Polymer systems can also be generated in which a desired active is chemically attached to the maleate structure that can undergo hydrolysis in the body to release the active over time.

The following diagram is a possible schematic of such a process:

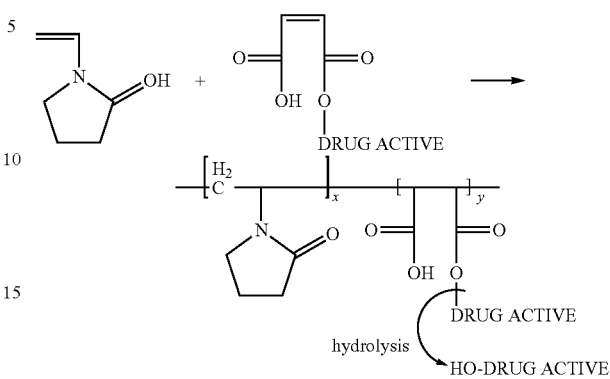

Also provided is a composition comprising a copolymer according to the invention for application into and/or onto a medical device. More specifically, compositions relating to medical device coatings to improve or alter coating lubricity or improve the interfacial adhesion between the copolymer coating and specific medical device. Preferred copolymers are VP-dialkyl maleate copolymers and VP-alkyl maleate copolymers. Alkyl groups based on hydrocarbon chains improve the interfacial adhesion to hydrocarbon based substrates such as polypropylene and polyethylene. Alkyl groups based on fluorocarbon chains improve the interfacial adhesion to fluoro-based substrates such as Teflon. In addition, maleates possessing reactive side chains such as olefin groups are of specific interest because such systems can be post-cured to give crosslinked coating systems having increased robustness and functionality.

A further aspect of the invention relates to the use of a polymer as provided herein as Lower Critical Solution Temperature (LCST) materials in water and applications there of. It has been discovered that many of the water soluble copolymer systems incorporating hydrophobic alkyl maleates and/or dialkyl maleates possess a LCST, that is the polymer phase inverts from being water soluble at low solution temperatures to water insoluble at higher solution temperatures. This phase inversion can be fine-tuned to occur at a specific temperature, for example at the body temperature of around 37° C. For such polymers, aqueous based medical preparations can be formulated that outside the body the system is soluble, but once injected/placed in the body the polymer under goes phase inversion at the higher temperature to form a solid-like implant. Such implants can be of great interest for the delivery of actives and/or for other applications. The ability to make bioresorbable polymer systems that have the ability to release a drug or active over time are possible. The drug or active release can be controlled by either complexation with the polymer, physical entrapment of the material during the phase change associated with the LCST and/or hydrolysis of the material over time as previously discussed. There is also considerable interest in such materials for industrial applications, especially in oil-field additives in which large phase transitions to generate viscosity at set temperatures/pressures are desirable.

Still further, the invention provides an antimicrobial or antifouling composition (coating) comprising a copolymer according to the invention. Hydrophobically modified copolymers generated by the addition of dialkyl maleates and alkyl maleates seem to have a significant effect at retarding microbial growth. Copolymers based on the incorporation of N,N-dialkylamino dialkyl maleates and their ammonia salts, specifically the halogen and zwitterionic species show both antimicrobial and antifouling attributes All of the compositions, methods and experiments disclosed and claimed herein can be made and executed without undue experimentation in light of the present invention. While the compositions, methods and experiments of this invention have been described in terms of preferred embodiments, it will be apparent to those skilled in the art that variations may be applied to the compositions and methods and in the steps or in the sequence of steps of the method described herein without departing from the concept, spirit and scope of the invention. All modifications and applications apparent to those skilled in the art are deemed to be within the spirit, scope and concept of the invention as defined by the appended claims.

LEGEND TO THE FIGURES

FIG. 1: Humidity resistance of wool tresses treated with 3% aqueous polymer solutions. For details, see Example 10.

EXPERIMENTAL SECTION

The following table outlines the results for examples 1, 2 and 3 of U.S. Pat. No. 2,980,654 in which VP is polymerized with di-2-ethylhexyl maleate at varying mole ratio's using precipitation polymerization.

| Example | Mole % monomer added | | % Nitrogen content in polymer | | % Difference from actual vs. predicted |
|---|---|---|---|---|---|
| | VP | maleate | Actual | Predicted | |
| 1 | 98.3 | 1.7 | 11.5 | 12.0 | 4.2% low |
| 2 | 96.5 | 3.5 | 11.5 | 11.4 | 0.9% high |
| 3 | 92.4 | 7.6 | 9.34 | 10.1 | 7.5% low |

As can be seen from the table, the actual nitrogen content differs substantially from the predicted value based on the monomer additions. The effects of this observation are: (1) the precipitation polymerizations are causing preferred compositions to be obtained that are independent of the actual monomer feeds, (2) deviation between the actual and predicted values means that substantial unreacted monomer must exist that is removed during the filtering/separation process and (3) the polymer properties are compromised and difficult to assess and predict based on this polymerization method as defined in U.S. Pat. No. 2,980,654.

It has now been discovered that when the polymerization reaction is conducted by solution polymerization, and preferably by the continuous feeding of a monomer mixture, vinyl lactam copolymers containing a desired fraction of maleate can be efficiently synthesized to give excellent biomaterials with desirable film properties. Examples 1, 2, 3 and 4 herein below represent VP copolymers containing 50 mole % di-2-ethylhexyl maleate, 25 mole % di-2-ethylhexylmaleate, 48 mole % dibutyl maleate and 25 mole % dibutyl maleate, respectively. All resultant dry polymer films were essentially non-tacky, clear and continuous. An materials showed excellent solubility in many skin care oils that when dissolved in and applied to the skin resulted in flexible continuous films having no negative aesthetics. For comparison, example 3162-197 of U.S. Pat. No. 2,999,853, a 1:1 copolymer of VP and dibutyl maleate, results is a "tacky, viscous liquid" polymer product.

EXAMPLES

Example 1

Polymerization of VP with di-2-ethylhexyl maleate in Isopropyl Acetate Solvent 29.5 g VP, 90.5 g di-2-ethylhexyl maleate and 280 g isopropyl acetate were placed in a 1000 ml three-neck round bottom flask fitted with a mechanical stirrer and cooling condenser. The reaction solution was inerted under moderate mixing with argon gas and heated to 80° C. after which 0.2335 g. 2,2'-azodi(isobutyronitrile) was added. After 3 hours, another 0.2234 g 2,2'-azodi(isobutyronitrile) was added. The reaction was allowed to react at 80° C. for a total of 18 hours. After the 18 hours, an additional 0.1828 g 2,2'-azodi(isobutyronitrile) was added, the temperature raised to 100° C. and the reaction reacted an additional 5 hours. The reaction was then cooled to room temperature and the viscous clear polymeric solution was discharged.

The resulting 30% solid's solution gave crystal clear, flexible films after drying that possessed no water solubility, but were highly soluble in various cosmetic skin care oils. The solubilized polymer when applied to the skin resulted in the formation of a soft and flexible film once the cosmetic oil was absorbed by the skin. The resultant film behaved as a sort of "second skin" that was both substantive and continuous having no negative aesthetics. The film enhanced the natural water barrier properties of the skin.

Such systems are expected to have potential application as water-proof and/or skin protectant polymers to keep desired actives on the skin surface from washing off (e.g. UV protectant) or "boost" the natural barrier properties of the skin to maintain proper hydration and/or limit penetration of undesirable compounds.

Example 2

Polymerization of VP with di-2-ethylhexyl maleate in Ethanol 74.25 g VP and 75.75 g di-butyl maleate were mixed together to give a clear solution (monomer mix). 50 g of this mix was added to a three-neck 1000 ml round bottom flask fitted with a mechanical stirrer, two dropping funnels, a condenser and 90 g ethanol. To the remaining 100 g monomer mix was added 50 g ethanol and placed in one of the dropping funnels. In the second dropping funnel was added a solution containing 0.73 g 2,2'-azodi(2-methylbutyronitrile) dissolved in 10 g ethanol. The entire reaction set-up and reactants were inerted with argon gas and the temperature raised to 75° C. Upon reaching 75° C., the monomer mix solution feed was added over a period of 2 hours and the initiator solution added over a period of 3 hours. The reaction was allowed to proceed for a total of 18 hours at 75° C. and then the temperature was raised to 85° C. and further reacted under slight reflux for an additional 2 hours. The polymer solution was cooled and discharged.

Glass slides were coated with the polymer solution and resultant dry films were clear, relatively hard and showed no water solubility. The resultant polymer had a K-value of 28 and both residual monomers were below 1000 ppm. The resultant polymer was readily soluble in a various natural based and synthetic skin care oils such as sun flower oil and $C_{12-15}$ alkyl benzoate.

Example 3

Polymerization of VP with Dibutyl Maleate in Ethanol 51.75 g VP and 98.25 g di-butyl maleate were mixed together to give a clear solution (monomer mix). 50 g of this mix was added to a three-neck 1000 ml round bottom flask fitted with a mechanical stirrer, two dropping funnels, a condenser and 90 g ethanol. To the remaining 100 g monomer mix was added 50 g ethanol and placed in one of the dropping funnels. In the second dropping funnel was added a solution containing 0.60 g 2,2'-azodi(2-methylbutyronitrile) dissolved in 10 g ethanol. The entire reaction set-up and reactants were inerted with argon gas and the temperature raised to 75° C. Upon reaching 75° C., the monomer mix solution feed was added over a period of 2 hours and the initiator solution added over a period of 3 hours. The reaction was allowed to proceed for a total of 18 hours at 75° C. and then the temperature was raised to 85° C. and further reacted under slight reflux for an additional 2 hours. The polymer solution was cooled and discharged.

The resultant 50% solid's polymer solution was clear. The resultant dry films were crystal clear, relatively hard and showed no water solubility or uptake. The polymer films could be completely submersed in water and the clarity was not compromised. The resultant polymer had a K-value of 20 and both residual monomers were below 1000 ppm. The resultant polymer was readily soluble in a various natural based and synthetic skin care oils such as: sun flower oil and $C_{12-15}$ alkyl benzoate.

Example 4

Polymerization of VP with Dibutyl Maleate in Ethanol 88.5 g VP and 61.5 g di-butyl maleate were mixed together to give a clear solution (monomer mix). 50 g of this mix was added to a three-neck 1000 ml round bottom flask fitted with a mechanical stirrer, two dropping funnels, a condenser and 90 g ethanol. To the remaining 100 g monomer mix was added 50 g ethanol and placed in one of the dropping funnels. In the second dropping funnel was added a solution containing 0.84 g 2,2'-azodi(2-methylbutyronitrile) dissolved in 10 g ethanol. The entire reaction set-up and reactants were inerted with argon gas and the temperature raised to 75° C. Upon reaching 75° C., the monomer mix solution feed was added over a period of 2 hours and the initiator solution added over a period of 3 hours. The reaction was allowed to proceed for a total of 18 hours at 75° C. and then the temperature was raised to 85° C. and further reacted under slight reflux for an additional 2 hours. The polymer solution was cooled and discharged.

The resultant 50% solid's polymer solution was clear. The resultant dry films were crystal clear, hard and water insoluble. Though not water soluble, the polymer films turned opaque when submersed in water. The resultant polymer had a K-value of 29 and both residual monomers were below 1000 ppm.

Example 5

Polymerization of VP with Dibutyl Maleate in Ethanol 142.5 g VP and 7.5 g di-butyl maleate were mixed together to give a clear solution (monomer mix). 50 g of this mix was added to a three-neck 1000 ml round bottom flask fitted with a mechanical stirrer, two dropping funnels, a condenser and 90 g ethanol. To the remaining 100 g monomer mix was added 50 g ethanol and placed in one of the dropping funnels. In the second dropping funnel was added a solution containing 0.85 g 2,2'-azodi(2-methylbutyronitrile) dissolved in 10 g ethanol. The entire reaction set-up and reactants were inerted with argon gas and the temperature raised to 75° C. Upon reaching 75° C., the monomer mix solution feed was added over a period of 2 hours and the initiator solution added over a period of 3 hours. The reaction was allowed to proceed for a total of 18 hours at 75° C. and then the temperature was raised to 85° C. and further reacted under slight reflux for an additional 2 hours. The polymer solution was cooled and discharged.

The resultant 50% solid's polymer solution was clear. The resultant dry films were crystal clear, hard and water soluble. The resultant polymer had a K-value of 53 and both residual monomers were below 1000 ppm. Water based Carbopol™ thickened hair styling gels utilizing the experimental polymer showed improved high humidity curl retention when compared to conventional PVP based gels.

Example 6

Polymerization of VP with 2-(N,N-diethylamino)ethyl octadecyl maleate 85.0 g VP and 15.0 g 2-(N,N-diethylamino)ethyl octadecyl maleate were mixed together to give a clear solution (monomer mix). 30 g of this monomer mix was added to a three-neck 1000 ml round bottom flask fitted with a mechanical stirrer, two dropping funnels, a condenser and 60 g ethanol. To the 70 g remaining monomer mix was added 30 g ethanol and the resultant solution was placed in one of the dropping funnels. In the seconds dropping funnel was added the initiator solution consisting of 0.75 g 2,2'-azodi (2-methylbutyronitrile) dissolved in 10 g ethanol. The entire reaction set-up and reactants were inerted with argon gas and the temperature raised to 75° C. Upon reaching 75° C., both the monomer mix and initiator solutions were added over a period of 1.5 hours. The reaction was allowed to proceed for a total of 15 hours at 75° C. and then cooled and the polymer solution discharged.

The resultant 50% solid's polymer solution was a viscous, hazy, slightly yellow in color solution. The resultant polymer dry films were clear. There was no amine odor associated with the solution or films. Dilute aqueous solutions containing this polymer were colorless and opaque. The polymer behaved as a polymeric surfactant in aqueous solution as seen from the foam generated during mixing.

Example 7

Quaternization of Example 5 Polymer

To 53.80 g of the resultant ethanol polymer solution obtained from example 5 was added 1.17 g diethylsulfate. The mixture was reacted at 90° C. for 5 hours and cooled. The resultant material was a viscous hazy solution.

Dilute aqueous solutions containing the quaternized polymer were colorless and crystal clear. The polymer possessed surfactant attributes as seen from the significant foam generated during mixing.

Example 8

Comparative Polymerization of VP with Diethyl Fumarate 99.0 g VP and 51.0 g di-ethyl fumarate were mixed together to give a clear solution (monomer mix). 50 g of this mix was added to a three-neck 1000 ml round bottom flask fitted with a mechanical stirrer, two dropping funnels, a condenser and 90 g ethanol. To the remaining 100 g monomer mix was added 50 g ethanol and placed in one of the dropping funnels. In the second dropping funnel was added a solution containing 0.83 g 2,2'-azodi(2-methylbutyronitrile) dissolved in 10 g ethanol. The entire reaction set-up and reactants were inerted with argon gas and the temperature raised to 75° C. Upon reaching 75° C., the monomer mix solution feed was added over a period of 2 hours and the initiator solution added over a period of 3 hours. The reaction was allowed to proceed for a total of 18 hours at 75° C. and then the temperature was raised to 85° C. and further reacted under slight reflux for an additional 2 hours. The polymer solution was cooled and discharged.

The resultant 50% solid's polymer solution was hazy at both warm and cool temperatures. Upon standing, the sample solution separated into three distinct layers with each layer representing its own unique polymer composition. This observation is representative of the formation of an inhomogeneous polymer product.

Example 9

Testing Results

Glass plates were coated with polymer solution (alcohol solutions) and allowed to dry at room temperature overnight. The following day, one drop of water (approximately 25 mg) was placed on the film and the various observations were noted as outlined in table 1.

TABLE 2

Test results on individual films

| Polymer[1] (mole %) | Ø[2] (mm) | Film Clarity | | | Moisture[3] Uptake |
|---|---|---|---|---|---|
| | | initial dry | wet | after drying | |
| 100% VP | 10 | clear | clear | clear | 26% |
| 97.5% VP/2.5% DBM | 9 | clear | clear | clear | 23% |
| 92% VP/8% DBM | 7 | clear | clear | clear | 20% |
| 75% VP/25% DBM | 5 | clear | opaque | clear | 8% |
| 52% VP/48% DBM | 4 | clear | clear | clear | 2% |
| Teflon comparison | 3 | | | | |

[1]VP—vinyl pyrrolidone, DBM—dibutyl maleate, 100% VP—Commercial PVP K30
[2]Diameter of water droplet on film measured after 30 sec. resonance time.
[3]Moisture uptake of films after 6 hours at 90% relative humidity, 25° C.

As can be seen from Table 2, the hydrophilicity of the PVP copolymers can be easily manipulated by the amount of DBM added to the polymers. The first indication that the hydrophilicity of the films can be controlled is by observing/measuring the water droplet spreading when placed on the dried films (Ø). The diameter of 10 mm is for the highly water soluble 100% VP homopolymer, while the water insoluble copolymer of 52% VP/48% DBM possesses a similar surface hydrophobicity to Teflon.

The water soluble high VP containing homopolymer and copolymers give clear films before during and after the water addition. Polymer 75% VP/25% DBM results in opaque wet clarity because though this polymer is not water soluble it does absorb enough water to result in opaque films which upon drying goes back to clear. Polymer 52% VP/48% DBM is very interesting in that the film clarity under wet conditions is due to the fact that the amount of water uptake/interaction is very small and water has a negligible effect on the polymer coating.

Finally, the actual moisture uptake for the series of VP/DBM copolymers follows the expected trend of significant moisture uptake for the VP/DBM copolymer series from a maximum of 26% moisture uptake for the VP homopolymer and only 2% uptake for the 52% VP/48% DBM copolymer.

Example 10

Formulation Results

The series of polymers discussed in experiment 6 were further tested in some simple formulation tests. FIG. 1 shows the formulation results for water soluble copolymers 97.5% VP/2.5% DBM and 92% VP/8% DBM as compared to 100% VP homopolymer. The results are an overview of the humidity resistance for the individual polymers on natural fibers. The results are based on application to wool tresses, but other natural fibers (e.g. hair) are expected to give similar behavior and trends.

As can be seen in FIG. 1, the highly water soluble 100% VP homopolymer quickly fails at high humidity in a time period of 6 hrs. The incorporation of a relatively small molar amount of DBM significantly improves the 6 hr. high humidity resistance to give resultant curl retentions of 92% and 100% for the 2.5 mole % and 8 mole % DBM incorporation, respectively. Surprisingly, wool tresses treated with the copolymer containing 8 mole % DBM possessed resultant curl retention of 80% even after a time period of 72 hrs at 90% RH.

Carbopol based gels utilizing the above polymers could be easily prepared and the resultant curl retention of these systems were excellent.

Example 11

Oil Containing Formulations

Oil based formulations can be easily formulated with polymers of this invention. The polymers can be formulated in 100% oil based formulations and in water-in-oil or oil-in-water based formulations. Because the hydrophobicity of the copolymers can be easily altered, polymers can be synthesized for application in either the oil or water phase or both phases. The copolymers are expected to have many of the same benefits/applications/properties as traditional VP homopolymers, but having application over a much broader product base to include lipophilic formulations and systems.

To a simple oil-in-water skin care lotion was added either example 5 polymer or example 6 polymer. The amount of actual polymer added was 1 weight % calculated on a 100% solids basis polymer. The resultant lotions utilizing either example 5 or example 6 polymers were significantly more viscous than the lotion without added example polymers.

The resultant lotions with added polymer were homogeneous and creamy and possessed no negative feel aesthetics when applied to the skin.

Example 12

Reaction of VP with Amyl Maleate

To a 500 ml 3-neck round bottom flask equipped with two dropping funnels and a mechanical stirrer was added 35 g ethanol. In the first dropping funnel was added 64.0 g VP, 36.1 g of amyl maleate and 55.0 g of ethanol. In the second dropping funnel was added 0.64 g 2,2'-azodi(2-methylbutyronitrile) dissolved in 10 g ethanol. The flask was placed in an oil bath and the oil bath was heated to 75° C. Upon reaching 75° C., both dropping funnels were started and the reactants/initiator solutions were added over a period of about 1.5 h. After the addition was complete the reaction was allowed to continue overnight at 75° C. The following morning a small amount of 2,2'-azodi(2-methylbutyronitrile) was added to the reaction product and the reaction continued for some additional hours and then cooled.

The resultant polymer was a highly viscous solution. Diluting the material in ethanol resulted in a clear solution that when coated onto glass resulted in a clear film. The film was found to be quite resistant to bacterial growth when challenged with microorganisms. Similar bacterial testing utilizing films of PVP homopolymer showed no such bacterial growth inhibition.

Example 13

To a 500 ml 3-neck round bottom flask equipped with two dropping funnels and a mechanical stirrer was added 35 g ethanol. In the first dropping funnel was added 60.0 g VP, 40.0 g of N,N-diethylamino-ethyl amyl maleate and 55.0 g of ethanol. In the second dropping funnel was added 0.63 g 2,2'-azodi(2-methylbutyronitrile) dissolved in 10 g ethanol. The flask was placed in an oil bath and the oil bath was heated to 75° C. Upon reaching 75° C., both dropping funnels were started and the reactants/initiator solutions were added over a period of about 1.5 h. After the addition was complete the reaction was allowed to continue overnight at 75° C. The following morning a small amount of 2,2'-azodi(2-methylbutyronitrile) was added to the reaction product and the reaction continued for some additional hours and then cooled.

The resultant viscous solution was diluted in ethanol to give a clear solution. The resultant films when dried on glass plates were clear. Bacterial growth studies on the resultant films showed significant inhibition of bacterial growth when compared with PVP homopolymer films.

The invention claimed is:

1. An N-vinyl lactam copolymer prepared by the process comprising reacting about 1-99 mole % of a vinyl lactam monomer (A), and about 99-1 mole % of a derivatized maleate monomer (B), wherein A/B≥1; A+B=100 mole %; and (A) and (B) are defined according to the following general formula:

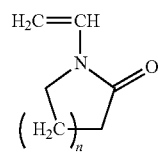
(A)

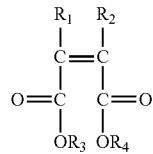
(B)

wherein n is 1 or 2;

$R_1$ and $R_2$ are each independently hydrogen or methyl; and $R_3$ and $R_4$ are each independently selected from hydrogen, alkyl groups, aryl groups, organometallic groups, and heteroalkyl and heteroaryl groups comprising at least one heteroatom other than carbon or hydrogen, with the proviso that both $R_3$ and $R_4$ are not hydrogen and $R_3$ and $R_4$ are selected so the resultant monomer (B) forms a weak di-monomer complex with (A); and wherein said reacting is performed by solution polymerization in a solvent or solvent mixture in which both the lactam monomer (A), the maleate monomer (B) and the resultant copolymer are freely soluble in, wherein the mixture of the monomers is fed to the reaction mixture as a pre-mixed monomer solution over a predetermined period of time, and wherein (A) and (B) form a weak di-monomer complex and the resultant copolymer is predominantly an alternating copolymer.

2. The copolymer according to claim 1, wherein the solvent is an alcohol, an ester, a skin care oil, emulsifier or emollient.

3. The copolymer according to claim 1, comprising the step of initiating the polymerization reaction using an azo initiator and/or organic peroxide system.

4. The copolymer according to claim 1, wherein the polymerization reaction is conducted at a temperature of between about 50°–150° C. for a period of 2 to about 20 hours.

5. The copolymer according to claim 1, wherein the polymerization reaction is conducted at an amount of solid of between about 10 wt. % and 70 wt. % based on the total weight of the reaction mixture.

6. The copolymer according to claim 1, wherein $R_3$ and/or $R_4$ comprises at least one heteroatom selected from the group consisting of oxygen, nitrogen, sulfur, silicon, metals and halogens.

7. The copolymer according to claim 1, having a Fikentscher K-value between 10 and 90.

8. The copolymer according to claim 1, having individual residual monomer levels of less than 1000 ppm.

9. The copolymer according to claim 1, wherein said alkyl is a linear or branched alkyl chain, the alkyl chain comprising 1-99 carbon atoms.

10. The copolymer according to claim 1, wherein $R_3$ and/or $R_4$ are selected from the group consisting of substituted or non-substituted alkyl, aryl, arylalkyl, alkoxy, aryloxy, alkylhydroxy, arylhydroxy, alkylaryloxy, alkylamino, arylamino, and alkylarylamino.

11. The copolymer according to claim 10, wherein $R_3$ and/or $R_4$ comprises a moiety selected from —(CH$_2$—CH$_2$—O)—, —(CH$_2$—CH(CH$_3$)—O)—, —(CH(CH$_3$)—CH$_2$—O)—, —(CH$_2$—CH(CH$_2$—CH$_3$)—O)—, —(CH(CH$_2$—CH$_3$)—CH$_2$—O)—, and —(CH(CH$_3$)—CH(CH$_3$)—O)—.

12. The copolymer according to claim 1, wherein $R_3$ and/or $R_4$ comprises at least one moiety selected from the group consisting of siloxane, ester, amido, fluoro, organometallic, amino and/or silyl groups.

13. The copolymer according to claim 1, wherein $R_3$ and/or $R_4$ comprises an anionic moiety.

14. The copolymer according to claim 1, wherein $R_3$ and/or $R_4$ comprises a cationic moiety.

15. The copolymer according to claim 14, wherein $R_3$ and/or $R_4$ comprises a primary, secondary, tertiary or quaternary amine.

16. The copolymer according to claim 1, wherein (A) is about 99-50 mole %.

17. The copolymer according to claim 1, wherein (B) is about 1-50 mole %.

18. The copolymer according to claim 7, wherein the Fikentscher K-value is between 20 and 60.

19. The copolymer according to claim 8, having individual residual monomer levels of less than 500 ppm.

20. The copolymer according to claim 9, wherein the alkyl chain comprises 1-50 carbon atoms.

21. The copolymer according to claim 9, wherein the alkyl chain comprises 1-30 carbon atoms.

22. The copolymer according to claim 13, wherein the anionic moiety is selected from the group consisting of carboxylic acid moieties, sulfonic acid moieties, phosphonic acid moieties, betaine moieties, and salts thereof.

23. The copolymer according to claim 14, wherein the cationic moiety is selected from the group consisting of amino moieties and ammonium salts.

24. A method for preparing an alternating N-vinyl lactam copolymer comprising
reacting about 1-99 mole % of a vinyl lactam monomer (A), and about 99-1 mole % of a derivatized maleate monomer (B), wherein (A) and (B) are defined according to the following general formula:

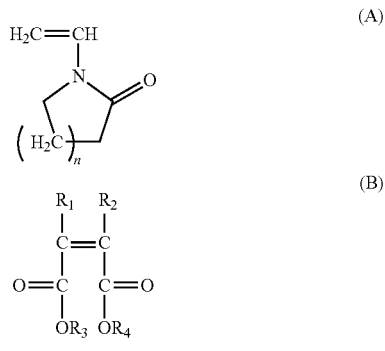

wherein n is 1 or 2;
$R_1$ and $R_2$ are each independently hydrogen or methyl;
$R_3$ and $R_4$ are each independently selected from hydrogen, alkyl groups, aryl groups, organometallic groups, and heteroalkyl and heteroaryl groups comprising at least one heteroatom other than carbon or hydrogen, with the proviso that both $R_3$ and $R_4$ are not hydrogen and $R_3$ and $R_4$ are selected so the resultant monomer (B) forms a weak di-monomer complex with (A),
wherein said reacting is performed by solution polymerization in a solvent or solvent mixture in which both the lactam monomer (A), the maleate monomer (B) and the resultant copolymer are freely soluble in, and wherein the mixture of the monomers is fed to the reaction mixture as a pre-mixed monomer solution over a pre-determined period of time,
and wherein A/B≥1 and A+B=100 mole %,
to form an N-vinyl lactam copolymer that is predominantly an alternating copolymer.

25. The method according to claim 24, wherein the mixture of the monomers is fed to the reaction mixture at a molar ratio of lactam monomer (A) to maleate monomer (B) of one or greater.

26. The method according to claim 24, wherein the solvent is an alcohol, an ester, a skin care oil, emulsifier or emollient.

27. The method according to claim 24, comprising the step of initiating the polymerization reaction using an azo initiator and/or organic peroxide system.

28. The method according to claim 24, wherein the polymerization reaction is conducted at a temperature of between about 50°–150° C. for a period of 2 to about 20 hours.

29. The method according to claim 24, wherein the polymerization reaction is conducted at an amount of solid of between about 10% and 70%.

30. The method according to claim 24, further comprising the step of exchanging the solvent or solvent mixture with a biocompatible solvent and/or isolating the copolymer via solvent drying.

31. The method according to claim 24, wherein $R_3$ and/or $R_4$ comprises at least one heteroatom selected from the group consisting of oxygen, nitrogen, sulfur, silicon, metals and halogens.

32. A reaction mixture comprising about 1-99 mole % of a vinyl lactam monomer (A), and about 99-1 mole % of a derivatized maleate monomer (B), wherein the mole % is based on the total moles of (A) and (B) in the reaction mixture, wherein A/B≥1; and (A) and (B) are defined according to the following general formula:

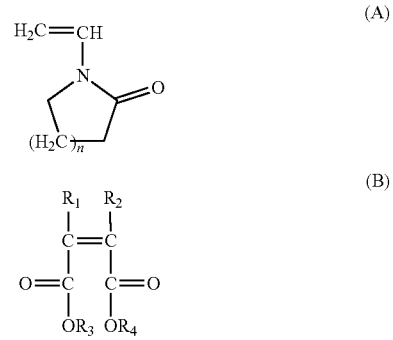

wherein n is 1 or 2;
$R_1$ and $R_2$ are each independently hydrogen or methyl; and
$R_3$ and $R_4$ are each independently selected from hydrogen, alkyl groups, aryl groups, organometallic groups, and heteroalkyl and heteroaryl groups comprising at least one heteroatom other than carbon or hydrogen, with the proviso that both $R_3$ and $R_4$ are not hydrogen and $R_3$ and $R_4$ are selected so the resultant monomer (B) forms a weak di-monomer complex with (A).

33. The reaction mixture according to claim 32, wherein $R_3$ and/or $R_4$ comprises at least one heteroatom selected from the group consisting of oxygen, nitrogen, sulfur, silicon, metals and halogens.

34. A personal care composition comprising a copolymer according to claim 1.

35. The personal care composition according to claim 34, being a hair care composition selected from the group consisting of a hair fixative product, hair styling product, hair conditioning product, and hair protectant product.

36. The personal care composition according to claim 34, being a skin care composition selected from the group consisting of water-in-oil or oil-in-water skin creams, day and night creams, eye creams, antiwrinkle creams, moisturizers, bleaching creams, vitamin creams, skin lotions, care lotions, hand and skin disinfectants and/or sanitizers, moisturizing lotions, personal hygiene care compositions, soaps, syndets, liquid washing, shower or bath preparations, nail care compositions, foot care compositions, sunscreens, repellents, shaving compositions, depilatories, and anti-acne compositions.

37. The personal care composition according to claim 34, being a preparation for decorative cosmetics selected from the group consisting of makeup, mascara, lipsticks, eye shadows, kohl pencils, eyeliners, blushers, powders, and eyebrow pencils.

38. A pharmaceutical composition comprising a copolymer according to claim 1.

39. A medical device comprising a copolymer according to claim 1.

40. An antimicrobial or antifouling composition comprising a copolymer according to claim 1.

* * * * *